US006080571A

United States Patent [19]

Prior et al.

[11] Patent Number: 6,080,571

[45] Date of Patent: *Jun. 27, 2000

[54] HIGHLY EFFICIENT PRODUCTION AND ISOLATION OF VIRAL PARTICLES UTILIZING TENTACLE ANION EXCHANGE

[75] Inventors: Christopher P. Prior, Wayne; David M. Weber, Phoenixville; Richard S. Gore, Southampton; James J. Harter, Media, all of Pa.

[73] Assignee: The Immune Response Corporation, Carlsbad, Calif.

[*] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 08/842,702

[22] Filed: Apr. 15, 1997

Related U.S. Application Data

[63] Continuation of application No. 08/613,920, Mar. 11, 1996, Pat. No. 5,661,023, which is a continuation of application No. 08/215,833, Mar. 22, 1994, abandoned.

[51] Int. Cl.⁷ ...................................................... L12N 7/02
[52] U.S. Cl. ........................ 435/239; 435/235.1; 210/660
[58] Field of Search ................................ 435/235.1, 239; 210/660

[56] References Cited

U.S. PATENT DOCUMENTS

| | | |
|---|---|---|
| 3,509,070 | 4/1970 | Lapidus et al. . |
| 3,655,509 | 4/1972 | Fields et al. . |
| 3,925,152 | 12/1975 | Porath et al. . |
| 4,647,773 | 3/1987 | Gallo et al. ............................. 435/239 |
| 4,725,546 | 2/1988 | Sakamoto et al. ...................... 435/239 |
| 5,661,023 | 8/1997 | Hrinda et al. ........................... 435/239 |

FOREIGN PATENT DOCUMENTS

| | | |
|---|---|---|
| 0 302 692 | 8/1988 | European Pat. Off. .......... C12N 7/02 |
| 0 459 842 A1 | 4/1991 | European Pat. Off. ....... A61K 39/21 |
| WO 92/10564 | 6/1992 | European Pat. Off. . |
| 61-051571 | 3/1986 | Japan . |
| 08195877 | 8/1990 | Japan . |
| WO 88/09670 | 12/1988 | WIPO ........................... A61K 39/21 |
| WO 9113906 | 9/1991 | WIPO . |

OTHER PUBLICATIONS

Schmid, G. et al., Continuous Hybridoma Suspension Cultures With and Without Cell Retention: Kinetics of Growth, Metabolism and Product Formation. J. Biotech. 22:31–40 (1992).

Tokashiki, Michiyuki et al., "High Density Culture of Hybridomas Recycling High Molecular Weight Components." *Advances in Animal Cell Biology and Technology for Bioprocesses.* 355–360 (1989).

Neuman, J.E. et al., "Human T cell Lymphotropic Virus Type III: Affinity Purification of Envelope and Gag Proteins; HTLV–III Protein Isolation and Characterization." Abstr. Ann. Meet. Am. Soc. Microbiol.: (1986) 86meet.324 T–43.

Li, J.K. et al., "Preparative Purification of Viral Polypeptides From Mouse Mammary Tumor Virus." J. Cell Biochem. (1987) Suppl. 11c, 181.

Billich, A. et al., "Purification, Assay and Kinetic Features of HIV–1 Proteinase; HIV virus–1 Recombinant Protease Isolation and Characterization; Gene Cloning and Expression in *Escherichia Coli*." Biol. Chem. Hoppe Seyler; (1990) 371, 3, 265–72.

Rittenhouse, J. et al., "Affinity Purification of HIV–1 and HIV–2 Proteases From Recombinant E. coli Strains Using Pepstatin–Agarose; ..." Biochem. Biophys. Res. Commun. (1990) 171, 1, 60–66.

Nalin, et al., "Purification and Characterization of Recombinant Rev Protein of Human Immunodeficiency Virus Type 1; ..." Proc. Natl. Acad. Sci. U.S.A. (1990) 87, 19, 7593–97.

Nalin, C.M. et al., "Purification and Biochemical Characterization of Recombinant HIV–1 Rev Protein; HIV–1 Virus–1 Protein Expression in *Escherichia Coli*." J. Cell. Biochem. (1990) Suppl.14D, 108.

Clarke, J.B. et al., "The Effect of Bioreactor Configuation on Production of HIV and Cell–Virus Interaction." Cytotech. 4:145–153 (1990).

Tolbert, William R. et al., "Perfusion Culture Systems for Production of Mammalian Cell Biomolecules." *Large–Scale Mammalian Cell Culture.* Academic Press, Orlando, Florida 97–119 (1985).

Fabry, L. et al., "High Density Microcarrier Cell Culture for Viral Vaccine Production." *Advances in Animal Cell Biology and Technology for Bioprocesses.* Butterworth & Co. Ltd. Great Britain 361–365 (1989).

Kloppinger, M. et al., "Flow Cytometric Process Monitoring of Hybridoma Cells in Batch and Perfusion Culture." *Advances in Animal Cell Biology and Technology for Bioprocesses.* Butterworth & Co. Ltd. Great Britain 125–127 (1989).

*Primary Examiner*—Leon B. Lankford, Jr.
*Attorney, Agent, or Firm*—Campbell & Flores LLP

[57] ABSTRACT

This invention is directed to a continuous process for producing viral particles comprising providing in a perfused growth medium a population of viable virally infected non-lytic cells, and removing medium containing said cells at a rate to maintain the steady-state log-phase growth of cells remaining in said perfused growth medium. The invention is also directed to a process for purifying retroviral particles comprising passing a solution comprising the retroviral particles and contaminants through an anion exchange resin, and eluting the retroviral particles from the resin.

7 Claims, 6 Drawing Sheets

LMW MARKERS (KD)

106 -
80 -
49.5 -
32.5 -
27.5 -
18.5 -

LANE #: 1 2 3 4 5 6

WESTERN BLOT OF INACTIVATED HIV-1 ANTIGENS

FIG. 4

LANES: 8 7 6 5 4 3 2 1

SDS-PAGE ANALYSIS

HIGHLY EFFICIENT PRODUCTION AND ISOLATION OF VIRAL PARTICLES UTILIZING TENTACLE ANION EXCHANGE

This application is a continuation of application Ser. No. 08/613,920, filed Mar. 11, 1996, now issued as U.S. Pat. No. 5,661,023, which is a continuation of Ser. No. 08/215,833, filed Mar. 22, 1994 now abandoned.

FIELD OF THE INVENTION

This invention is directed to a process for producing viral particles from a non-lytic cells, which viral particles are useful as immunogens and/or vaccines, using a perfusion bioreactor system. The invention is also directed to a process for isolating retroviral particles using anion exchange chromatography.

REPORTED DEVELOPMENTS

Classical laboratory procedures for producing significant quantities of viral particles from a non-lytic cells principally involve the expansion and pooling of multiple batch cultures. The scale-up methods are problematic as they require considerable safety measures and expenditures for workers, equipment and waste material management to meet governmental biohazard containment standards, particularly where highly infectious virus production is involved. Additionally, viral vaccines production generally involves culturing infected cells at low densities, which for low producing systems, such as the retrovirus HIV-1 (lentiviridae), results in relatively low viral titers.

The pandemic status of HIV infections has led to extensive efforts to prepare HIV and other retroviral particles for the construction of numerous antigens derived therefrom. PCT WO 88/09670 to Jonas Salk and Dennis J. Carlo is directed to the preparation of noninfective/inactivated HIV immunogens, hereinafter referred to as Salk-type immunogens, which are devoid of envelope glycoproteins gp 160 or gp 120. The usual method for preparing these immunogens and HIV vaccines (which include both HIV-1 and HIV-2) involves multiple batch culturing of HIV-infected cells and isolating HIV particles using inactivation, filtration and ultracentrifugation (isopycnic sedimentation on sucrose gradients) steps (hereinafter referred to as the "Classical Process") is shown in FIG. 1. The latter technique is particularly volume limiting, labor intensive and requires a high capital investment for scale-up. The method also only produces about 10 doses of Salk-type immunogen having a total protein content of about 100 $\mu$g/mL or 8–10 $\mu$g/mL by p24 based ELISA per 1 liter of cell culture suspension. Thus, the processing leading to the dosage form has not lent itself to industrial production, because of its low yield and the need for handling multiple unit operations of infectious fluids, not to mention the necessity of achieving a vaccine having an extremely high degree of purity that is suitable for administration to humans. Thus, safer, less labor intensive and more cost efficient scale-up processes with high resolution are needed for the production of viral particles, and more particularly scaled-up production.

Perfusion bioreactor systems are described as alternatives to traditional multiple batch cultures for producing high cell densities and their secreted biomolecules. W. R. Tolbert, et al., Perfusion Culture Systems for Production at page 97 in Large-Scale Mammalian Cell Culture, edited by J. Feder and W. R. Tolbert, Academic Press, Inc. (1985), disclose using perfusion bioreactor systems for producing high cell densities while removing metabolic wastes in a perfusion stream and partially harvesting cells in a harvest stream. W. R. Tolbert, et al., also disclose using perfusion bioreactor systems to produce and maintain high cell densities while concomitantly removing secreted biomolecules and metabolic wastes in a perfusion stream. G. Schmid, et al., J.Biotech., 22, 31 (1992) disclose that the use of a perfusion bioreactor system with and without partial retention of a hybridoma suspension culture produces nearly identical antibody concentrations and specific productivities, but effects an increase in the viable cell count and space-time yield by a factor of 2.5. M. Kloppinger, et al.: Flow Cytometric Process Monitoring of Hybridoma Cells in Batch and Perfusion Culture, at page 125 in Advances in Animal Cell Biology and Technology for Bioprocesses, edited by R. E. Spier, et al., Butterworth & Co. Ltd. (1989), disclose that a perfusion bioreactor perfuses IgG in cell free containing medium with a six fold higher production of IgG than as compared to batch cultures. M. Tokashiki, et al.; High Density Culture of Hybridomas Recycling High Molecular Weight Components, at page 355, in Advances in Animal Cell Biology and Technology for Bioprocesses, edited by R. E. Spier, et al., Butterworth & Co. Ltd. (1989), disclose using a perfusion bioreactor system to produce a high density culture of hybridomas with a concomitant retention of high molecular weight components produced by the hybridomas while perfusing low molecular weight substances, including metabolic wastes, from the culturing medium. None of these references, however, disclose or suggest using a perfusion bioreactor for the production of viral particles.

Viral particle production in bioreactor systems are described in the following references. L. Fabry, et at.; High Density Microcarrier Cell Culture For Viral Vaccine Production, at page 361 in Advances in Animal Cell Biology and Technology for Bioprocesses, edited by R. E. Spier, et al., Butterworth & Co. Ltd. (1989), disclose using a perfusion bioreactor for growing an anchorage-dependent cell line to confluency with a concomitant perfusion of metabolic wastes, followed by the infection of the cell line with polio virus generation. L. Fabry, et al., also disclose that the kinetics of viral replication and the specific rate of viral particle production for the perfusion bioreactor are similar to those prepared in conventional cultures. L. Fabry, et al., do not disclose or suggest using a perfusion bioreactor for the growth of a cell system with concomitant viral particle production. J. B. Clarke and J. B. Griffiths, Cytotechnology, 4, 145 (1990), disclose the operation of two bioreactor systems using suspension cultures for batch mode productions of HIV. J. B. Clarke and J. B. Griffiths also disclose operating a fixed-bed bioreactor system wherein HIV producing cells that are retained in a carrier are suspended in growth medium, removed therefrom and resuspended in fresh growth medium. J. B. Clarke and J. B. Griffiths, however, do not disclose producing viral particles in a perfusion bioreactor containing a growth medium and virally infected non-lytic cells under conditions wherein growth medium is perfused from the bioreactor, growth medium containing cells and the virus is harvested from the bioreactor, and fresh growth medium is added to the bioreactor.

Following the production of viral particles from a cell culture, processes for isolating viral particles, particularly retroviral particles, are fraught with problems. Conventional multiple batch cultures produce large volumes of solutions having low viral titers. The handling of these low viral titers in large solution volumes is a significant waste management problem. In addition, these solutions must be purified to a high degree of purity to remove significant amounts of cellular debris, metabolic wastes and growth medium factors from the desired viral particles. Furthermore, the culture medium typically contains a high percent of fetal bovine serum, as a growth factor, which is a complex mixture of components that adversely challenges isolation processes. The isolation of HIV retroviruses is particularly problematic since the viruses are produced in low titers in an expensive and high serum containing medium and its isolation requires multiple ultracentrifugation steps that are highly throughput limiting and labor intensive. Thus, high manpower needs, large amounts of purification materials, high maintenance equipment usage and significant floor space in an expensive BSL3 facility are needed for isolating retroviral particles. In addition, one needs to control extraneous substances in the growth medium in which the retroviral particles are produced. Consequently, an alternative cost effective and scaleable method for isolating retroviral particles is needed.

Numerous references disclose methods for isolating individual viral proteins. WO9113906 discloses fractionating the non-fusion recombinant HIV viral protein gp 120 by ion exchange chromatography and purifying the fraction exhibiting CD4 specific binding affinity by hydrophobic interaction and size-exclusion chromatography. U.S. Pat. No. 4,531,311 discloses separating recombinant HIV reverse transcriptase protein from contaminating cellular proteins by using a cation-exchange resin. JP61051571 discloses purifying a swine herpes virus antigen by its adsorbtion on an ionic exchange resin, followed by the antigen's selective elution using a buffer. C. M. Nalin, et al., Proc.Natl. Acad. Sci. U.S.A. 87(19) 7593 (1990) and C. M. Nalin, et al., J.Cell Biochem. Suppl. 14D, 108 (1990) disclose the purification of recombinant HIV Rev protein by ion exchange and gel filtration chromatography. J. Rittenhouse, et al., Biochem. Biophys.Res. Commun. 171(1) 60(1990) disclose purifying recombinant HIV-1 and HIV-2 proteases by ion exchange chromatography on Mono S,. followed by pepstatin-agarose chromatography. A. Billich, et al., Biol.Chem. Hoppe-Seyler 371(3) 265(1990) disclose purifying recombinant HIV-1 protease by cation exchange chromatography on Mono S., preceded by gel filtration chromatography on Superose R and ultrafiltration. J. K. K. Li, et al., J.Cell Biochem.Suppl. 11C, 181(1987) disclose the gradient-purification of mouse mammary-tumor virus, a B-type virus, followed by the disruption of the virus and the separation of the viral structural polypeptides using sequential affinity and ion exchange column chromatography. J. E. Newman, et al., Abstr. Annu.Meet.Am. Soc.Microbiol. 86 Meet., 329 T-43 (1986) disclose isolating HTLV-3 structural proteins by passage over a lentil lectin affinity resin, followed by further purification using HPLC ion exchange chromatography and gel filtration steps. These references, however, do not disclose or suggest that a retroviral particle, more particularly an HIV particle, may be purified by anion exchange chromatography.

Several references disclose the application of ion exchange chromatography to the purification of viral particles. EP 0302,692 discloses purifying hepatitis A virus (HAV) by anion exchange chromatography to remove DNA. JO2195877 discloses purifying a retrovirus or components thereof by their contact with a cellulose sulfate gel or crosslinked polysaccharide sulfate gel (cationic adsorbent) and subsequent elution therefrom. EP 0459,842 discloses using a cation exchange chromatography step to purify retroviral particles. These reference, however, do not disclose or suggest that a retroviral particle, more particularly an HIV particle, may be purified by anion exchange chromatography by the particles binding to the resin.

SUMMARY OF THE INVENTION

This invention is directed to a continuous process for producing viral particles comprising providing in a perfused growth medium a population of viable virally infected non-lytic cells, and removing medium containing said cells at a rate to maintain the steady-state log-phase growth of cells remaining in said perfused growth medium.

The invention is also directed to a process for purifying retroviral particles comprising passing a solution comprising the retroviral particles and contaminants through an anion exchange resin, and eluting the retroviral particles from the resin.

BRIEF DESCRIPTION OF THE FIGURE

FIG. 4 is a Western Blot that shows antigenic staining profiles of a lot of HIV-1 particles at concentrations of 0.1, 0.25, 0.5 and 1 μg/mM (using Human New York anti sera isolated from HIV infected patients) prepared by the perfusion bioreactor system and isolated using inactivation, filtration and anion exchange chromatography steps (lanes 2–5 respectively) and the staining profile for the reference standard lot of HIV-1 particles at a concentration 1 μg/mM prepared by the "Classical Process" (lane 6) relative to low molecular weight markers (lane 1).

DETAILED DESCRIPTION OF THE INVENTION

Figure 1:
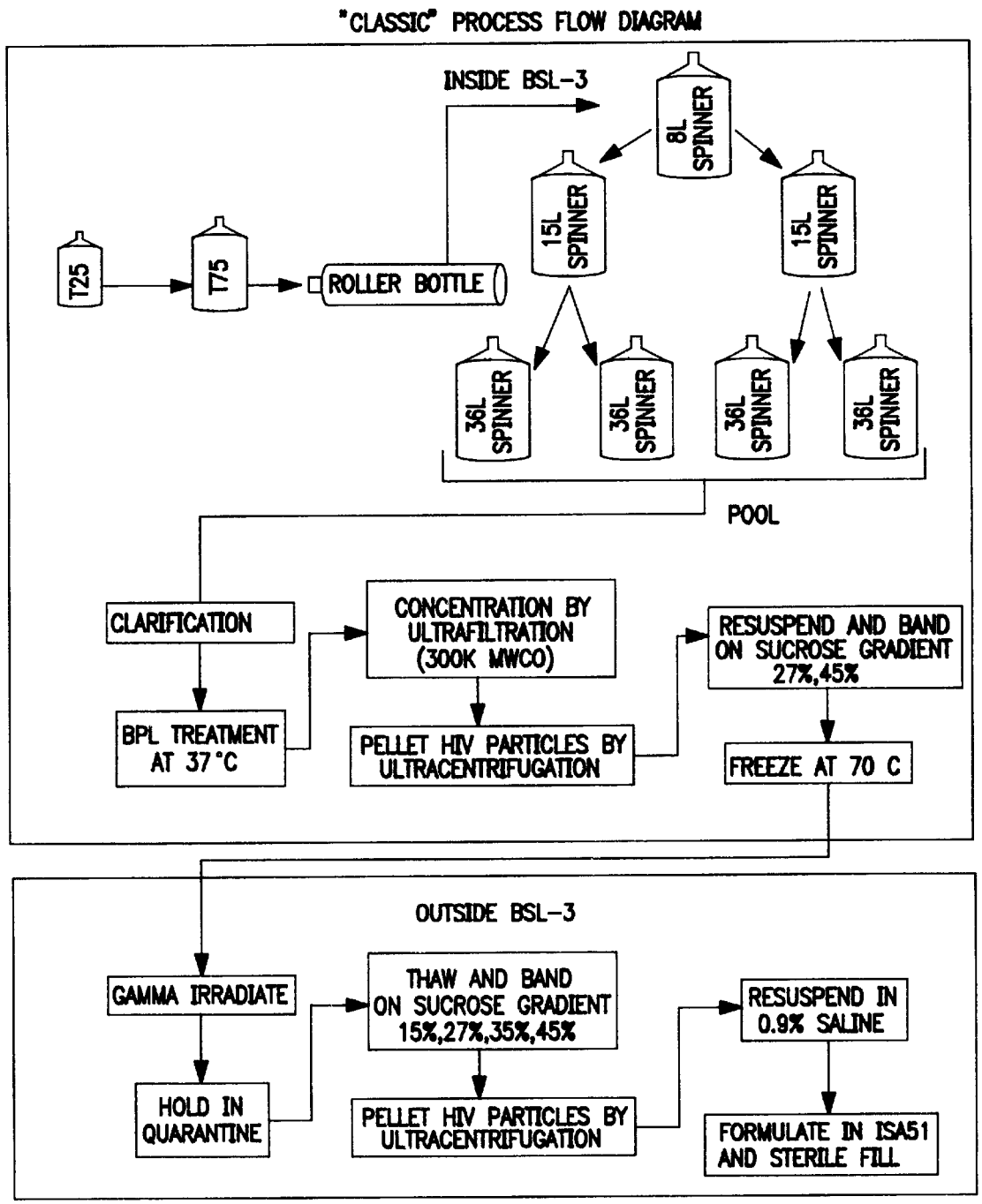
FIG. 1 is a diagram for obtaining HIV particles by the "Classical Process" having an upstream production component that uses a multiple batch culture system and a downstream isolation component that uses inactivation, filtration and ultracentrifugation steps.

As used above, and throughout the description of the invention, the following terms, unless otherwise indicated, shall be understood to have the following meanings:

Definitions

"Patient" includes human and other mammals.

"Viral particles" include complete virions (viruses), as well as related viral particles, but not single viral proteins. The source of the viral particles for cell culturing may be from a virally infected patient or viruses propagated in the laboratory, by repeated passage on susceptible cell systems. Examples of viral particles include capsids, core particles, virions depleted of one or more envelope proteins, virion envelopes without the nuclear capsid core, virion envelope fragments and defective or incomplete virions. A preferred viral particles are retroviral particles.

"Retroviral particles" means those viruses which contain RNA as their genomic material, including human immunodeficiency viruses (HIV), such as HIV-1 and HIV-2, HIV depleted of gp 120 and/or 160 proteins, HTLV-1, HTLV-2, AKR virus AKR-L#1, Moloney leukemia virus, and BLV. Preferred retroviral particles include HIV, HIV depleted of gp 120 and/or 160 proteins, HTLV-1 and HTLV-2, and more preferred is HIV-1.

"Cell system" includes T-lymphomas, HUT-78, H9, HZ 321, W/Fu fibroblast cell line 78A1, SC-1, human monocytes, CEM cell, and Molt-4 cells.

"Growth medium" means a solution containing a nutrient mixture that supports the growth and survival of a mammalian cell system. The growth medium may or may not contain serum or proteins.

"Tentacle anion exchange resin" means a resin wherein the portion thereof having the capacity to bind a negatively charge particle is situated at or near the end of a spacer moiety that is distal to the attachment site of the spacer moiety to the resin's backbone component. An example of a tentacle anion exchange resin is TMAE FRACTOGEL (tentacle anion exchange resin) from E. M. Merck.

Preferred aspects according to the invention in the process for preparing viral particles are as follows:

wherein viral particles present in said removed medium are separated from said cells wherein said medium containing said cells and said viral particles are removed before said cells reach stationary-state growth;

wherein said growth medium is refreshed at a rate defined by a removal rate of the cells;

wherein said medium containing said cells and said viral particles are continuously or intermittently removed;

wherein from about 20% to about 80% of said medium containing said cells and said viral particles is removed per day, more preferably about 20% to about 50% of said growth medium is harvested per day;

wherein said viral particles are retroviral particles, more preferably the retroviral particles are HTLV-1, HTLV-2, HIV-1, HIV-2 or HIV depleted of gp 120 and/or 160 proteins, and further preferably said retroviral particles are HIV-1;

wherein said growth medium is a serum-free medium; and/or wherein said cells are human T cell lymphomas chronically infected with HIV-1.

Preferred aspects for isolating retroviral particles according to the invention are as follows:

wherein said retroviral particles are HTLV-1, HTLV-2, HIV-1, HIV-2 or HIV depleted of gp 120 and/or 160 proteins, more preferably wherein said retroviral particles are HIV depleted of gp 120 or gp 160 proteins;

wherein said eluting is carried out with about 0.6 to about 2 M NaCl, and more preferably said eluting is carried out with about 1 M NaCl;

wherein said anionic exchange resin is a tentacle anion exchange resin;

wherein said anionic exchange resin is TMAE FRACTOGEL (tentacle anion exchange resin); and/or wherein said purifying further comprises washing said resin with about 0.1 to about 0.55 M NaCl after said contacting and before said eluting.

Perfusion bioreactor systems usable according to the invention are configured to permit the retention of cells and viral particles in the bioreactor, to maintain a continuous perfusion of growth medium into and out of the bioreactor and to facilitate the harvesting (removing) of growth medium containing the cells and viral particles and refreshing of the growth medium (replacement of harvested growth medium with fresh growth medium). These bioreactors may be configured for internal and/or external perfusion relative to the bioreactor. A bioreactor system used according to the invention is shown in FIG. 2.

Figure 2:
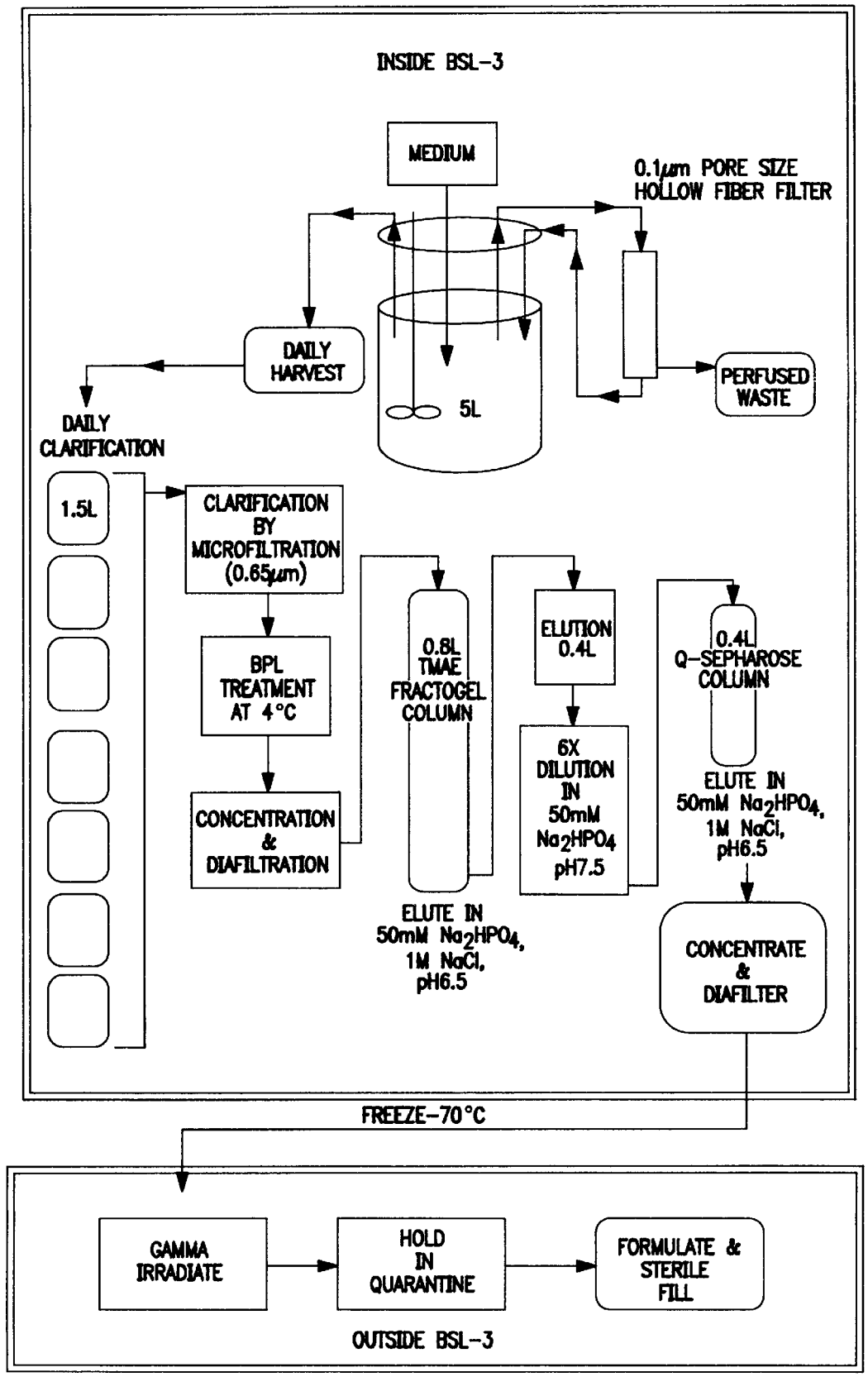
FIG. 2 is a diagram for obtaining HIV particles by a process having an upstream production component that uses a perfusion bioreactor system and a downstream isolation component that uses inactivation, filtration and anion exchange chromatography steps.

The perfusion bioreactor system in FIG. 2 uses an external hollow fiber perfusion filter, with a piping module that recirculates cells back into the reactor from the retentate side of the filter membrane while growth medium containing waste products is withdrawn from the permeate side. The pore size of the filter is selected such that there is a complete or nearly complete retention of viral particles within the bioreactor, such as using a 500 kd MWCO® ultrafilter to a $0.1\mu$ pore size filter. Under control of a level sensor, a feed pump supplies fresh medium to maintain a constant volume inside the reactor. Cells are aseptically harvested through a diptube reaching below the liquid surface in the bioreactor. This system lends itself to high density cultures where it is crucial to maintain cells with high viability and growth rate, and to minimize debris in the bioreactor.

The bioreactor is adjusted to operate with a perfusion rate that supports the optimal cell density for a cell system before cell growth rate and viability decline significantly. Furthermore, to maintain optimal cell density, growth rate and viability, the growth medium must be harvested to "cut-back" the cell density to a level such that the cell density does not exceed the maximal density. The cells should be harvested before the cells reach stationary-state growth, and the cells should substantially exhibit a steady-state log-phase growth. The harvest can be continuous or intermittent. The percent of growth medium volume which should be harvested is approximately equal to the growth rate of the cell system ($\mu$) which is equal to $[\ln (\text{final cell density/initial cell density})]/(\text{time}_{final} - \text{time}_{initial}) \times 100$. For example, if the cell density increases by 30% every 24 hours, then 30% of the reactor volume should be harvested per day. For, daily harvests from about 20% to about 80% of the growth medium is harvested per day, more preferably about 20% to about 50% of the growth medium is harvested per day. This harvest also reduces debris in the bioreactor by removal of dead cells before they lyse. Furthermore, a daily harvest of the growth medium provides for the removal of viral particles in a single, concentrated product stream.

The perfusion filter used according to the invention has a pore size that supports a molecular weight cutoff that retains both the cell system and viral particles and maintains perfusion. The determination of the molecular weight cutoff is determined by the size of the viral particles that are to be retained. For HIV particle production according to the invention, Sepracor, Inc., Type A hollow fiber filters having 0.1μ pores and A/G Technology, Inc., hollow fiber ultrafilters with a 500,000 dalton molecular weight cutoff retain both the cell system and viral particles and maintain a full perfusion flux rate for average periods of 5–10 days before fouling affects the perfusion rate. As an alternative to having a single filter, a manifold of perfusion filters, used sequentially, support perfusion during a continuous viral production run, e.g., a manifold of 5 perfusion filters supports a continuous bioreactor run of approximately 5 weeks.

The perfusion filter component is also operable in such a way as to provide for the automatic regeneration of a filter, such as by an aseptic in situ cleaning of a perfusion filter with a basic solution, such as aqueous sodium hydroxide. When the filter's transmembrane pressure reaches a certain set point due to the beginning of fouling, a controller stops the recirculation of growth medium containing the cell system and viral particles through the filter, purges the filter with phosphate buffered saline (PBS) to remove cells, cleans the filter with a basic solution, and flushes the filter with PBS prior to returning the filter to service. This regeneration step provides for operating a filter on a high cell density bioreactor for about 3 months at a continuous maximum perfusion rate of about 4 reactor volumes per day. This level of automation reduces operator decision and manipulation as well as reducing costs associated with hollow fiber usage. The Trio clarification system (Sepracor, Inc.) is modified for this filter regeneration step.

The inoculum for the bioreactor is prepared according known methods for tissue culturing. For example, a cell system is place in a T75 tissue culture flask containing growth medium capable of supporting its growth, such as RPMI 1640/10% fetal bovine serum to initiate growth. The culture is subsequently expanded into roller bottles to provide at least about $2\times10^5$ cells/mL in the bioreactor. Higher seeding densities are preferred in order to minimize the growth phase to about 5 to about 10 days. Following the inoculation of the bioreactor with an HIV infected cell system, when the cell density reaches about $1\times10^6$ cells/mL, perfusion is started at about one reactor volume/day. At about $2\times10^6$ cells/mL, perfusion is increased to about two reactor volumes/day and at about $4\times10^6$ cells/mL, perfusion is increased to the maximal rate of 4 volumes/day. For 4 reactor volumes/day will support a maximal density of more than $8\times10^6$ cells/mL.

The bioreactor harvests containing cells and viral particles may be isolated according to known methods.

Retroviral particles are also isolated according to the invention. Initially, bioreactor harvests containing cells and retroviral particles are clarified using a filter having about 0.5 to about 1.7, preferably about 0.7 to about 1.5, more preferably about 1.2μ pore size to pass the retroviral particles and to retain cells and other debris. The clarified harvests of infectious retroviral particles are pooled and well mixed to ensure homogeneity.

The infectious retroviral particles are then subjected to inactivation by adding beta-propiolactone (BPL) (at about 0.25 mL BPL/L of supernatant) with continues stirring, followed by incubation the mixture for about 2° C. to about 8° C., preferably at about 4° C. to about 6° C. for about 18 to about 24 hours. The pool is then raised to 37° C. and held at this temperature for about 2 to about 5, preferably about 3 to about 4 hours to hydrolyze residual BPL. This step serves to chemically reduce infectivity of the virus by alkylating the various structural components such as lipids, proteins, nucleic acid, etc. BPL inactivation is not considered to be a definitive inactivation step, and as such the BPL treated retroviral particles should still be considered infectious and treated as such.

The solution containing the BPL treated retroviral particles is then concentrated about 10 to about 20 fold by tangential flow ultrafiltration using a polysulfone 300,000 MW cutoff membrane. The concentrate is then diafiltered against about 5 to about 10 volumes of PBS, at pH about 7 to about 8, preferably about 7.5, to provide the required buffer conditions for the subsequent anion exchange chromatography step and to increase the binding capacity during that chromatography step. This step serves to remove more than 90% of the albumin in the permeate while retaining the retroviral particles.

The diafiltered solution containing the retroviral particles is passed through one or more columns containing anion exchange resin, such as TMAE FRACTOGEL tentacle anion exchange resin; (E. M Merck) or Q-SEPHAROSE (quaternary amine beaded agarose). A tentacle anion exchange resin is preferred since the site thereon for binding anionic particles have the highest binding capacity for viral sized particles and, thus yield the highest fold purification compared to non-tentacle anion exchange resins. The high flow rates of the anion exchange resins facilitate rapid purification of large lot sizes in one unit operation compared to isopycnic sedimentation requiring the use of multiple ultracentrifuges. The rapid turn around time of columns allows equipment to return to storage making space available for other operations including ultrafiltration procedures. Importantly, the resins were selected for their stability to NaOH which is used to strip columns of tightly bound biological material, for sanitization, decontamination, and inactivation of endotoxin.

The anionic exchange resin should also facilitate the removal of contaminants while preserving the structural integrity of the viral particle undergoing purification. Anionic contaminants, such as DNA and endotoxin, co-concentrate with the viral particles, but these particular contaminants bind tenaciously to the resins permitting the selective elution of the viral particles by a high salt concentration, such as about 1.0 M NaCl. Each anion exchange chromatography step achieves at least a two log reduction or four logs for the cumulative reduction of anionic contaminants for two steps. Size exclusion HPLC, Western blot and SDS-PAGE analyses of the eluted viral products also do not show detectable structural alteration in the eluted viral particles for at least about 24 hours. Storage of the eluted viral particles in the elution buffer for several days does result in detectable structural alteration. Thus, the immediate dilution of the eluent to prevent dissociation phenomenon and to maintain consistency of the structural components is suggest, particularly for maintenance of the immunogenic profile when the product is emulsified in Incomplete Freund's Adjuvant.

Where a diafiltered solution containing the retroviral particles is passed through a column containing the tentacle anion resin TMAE FRACTOGEL (tentacle anion exchange resin), the resin is subsequently washed with about 0.1 to about 0.55 M, preferably about 0.3 to about 0.5 M, more preferably about 0.5 M NaCl at pH about 6 to about 7.5, preferably pH about 6.2 to about 6.8, more preferably pH about 6.5 and eluted using a higher NaCl concentration at about 0.6 to about 2 M, preferably about 0.8 to about 1.4 M, more preferably about 1 M NaCl at about 6 to about 7.5, preferably pH about 6.2 to about 6.8, more preferably pH about 6.5. The column may be sanitized with about 0.7 to about 1.3 M, preferably about 1 M NaOH.

The eluted solution containing the retroviral particles, particularly HIV, is sufficiently diluted about four to about eight fold, preferably six fold, to reduce the salt concentration to within the range about 0.05 to about 0.25 M, preferably about 0.1 to about 0.2 M NaCl at pH about 6.2 to about 7.7, preferably pH about 6.6 to about 7.5, to prevent the partial disassembling of the HIV-1 particles when exposed to the eluant's higher NaCl concentration for prolonged periods of time, such as greater than about 18 hours. This first column is the most critical and efficient purification step in the process achieving about a 40 fold purification to total protein ratio. SDS-PAGE analysis shows the bulk of the medium components are in the column flow through, more contaminants are removed by the wash the NaCl wash, and for HIV particles a recognizable protein pattern compared to a HIV-1 reference standard is determinable from the elution fraction.

Following dilution and mixing to ensure homogeneity, the solution of retroviral particles is applied to a second anion exchange resin, such as a Q-SEPHAROSE (quaternary amine beaded agarose) column. The second application is carried out using about one half the amount of resin compared to the use of the first resin, if the first resin were a tentacle anion exchange resin. Chromatography using Q-SEPHAROSE (quaternary amine beaded agarose) is carried out by washed the resin with from about 0.3 to about 0.8 M, more preferably about 0.6 M NaCl and viral particles are eluted using an eluant as described in the first resin application.

Viral particles eluant fractions of about 1 M, following the second anion exchange chromatography step, are concentrated 5 fold using an ultrafiltration plate and frame system containing a polysulfone 300,000 MW cut-off membrane. The concentrate is then diafiltered against saline to reduce the salt concentration to isotonic strength and to reduce phosphate levels in preparation for product formulation. The purified product is frozen at −70° C., and is subjected to cobalt irradiation (about 2 to about 4.5 megarads) for approximately 24 hours. This procedure serves as the definitive inactivation step by shearing nucleic into pieces of approximately 200 base pairs as determined by PCR analysis.

The product is formulated diluted with 0.9% saline for injection to achieve the required concentration of antigen (p 24 concentration), and is aseptically mixed with an equal volume of Incomplete Freund's Adjuvant using a shaker device for approximately 1 hour. The final material (bulk immunogen), now ready for aseptic fill, appears as a viscous off-white emulsion.

The present invention is further exemplified but not limited by the following examples which illustrate the processes according to the invention.

The host cell line used for production of viral particles is a chronically infected with T-lymphoma designated IPL 1 for which a serum-free growth medium (IMAT) is developed that sustains good virus production and comparable growth rates to cells cultured in 10% fetal bovine serum (FBS). IMAT is formed by adding components from the following list.

| Component | Conc. |
| --- | --- |
| Transferrin, Human (HOLO) HI (Miles) | 0.010 g/L |
| Insulin, Human recombinant, Zn | 0.010 g/L |
| Albumin, Human Serum (25%) | 5.0 mL/L |

-continued

| Component | Conc. |
| --- | --- |
| Cholesterol | 0.00045 g/L |
| DL-Alpha-Tocopherol Acetate | 0.0002 g/L |
| Cod Liver Oil | 0.001 g/L |
| Linoleic Acid | 0.000021 g/L |
| DL-Alpha-Lipoic Acid | 0.0000515 g/L |
| Tween 80 | 0.0025 mL/L |
| Ethanolamine F.B. | 0.000611 g/L |
| Pluronic F-68, NF Grade | 1.000 g/L | to RPMI 1640 containing 4 g/L of glucose and 0.3 g/L of L-glutamine. The reduction in the protein content of the serum-free medium helps in the efficiency of downstream processing.

Cells from the Manufacturer's Working Cell Bank (MWCB) are expanded in T flasks followed by spinners or roller bottles, progressing from T25→T75→T150→850 cm$^2$ roller bottle, to provide inoculum for the bioreactor. At the time of seeding, at a minimal density of $2\times10^5$ cells/mL, cells are in exponential growth with viabilities above 65%. These requirements are necessary in order to minimize the lag phase in the bioreactor to within five days following initial seeding. When the cells start to grow, 24 hours after seeding, and achieve a density between $5\times10^5$ to $9\times10^5$, a continuous supply of fresh medium is provided, and spent medium is removed on a continuous basis. The rate of medium exchange commences at approximately 0.5 reactor volume/day and is increased to 4 reactor volumes/day when cell density reaches about 2 to about $4\times10^6$ cells/mL. In this continuous state of perfusion, cell densities of about $8\times10^6$ are achieved, which is a consequence of delivering nutrients and removing waste products on a continuous basis. Therefore, perfusion typically achieves about 10 to about 20 fold higher cell density than the average daily cell density obtained in spinners, where cells are grown in a batch mode.

The configuration of the reactor that permits retention of cells while maintaining continuous perfusion is presented in FIG. 2. The principle involves an external hollow fiber filtration device with a piping module that recirculates cells back into the reactor from the retentate side of the filter membrane while spent medium is withdrawn from the permeate side. Use of a hollow fiber filter, with a 0.1 micron pore size, for the removal of waste products results in almost complete retention of viral particles within the bioreactor, thus facilitating removal of the viral particles in the daily harvest along with cells. A feed pump supplies fresh medium which maintains constant volume under control of a level sensor. We have determined that for the IPL 1B MWCB, a perfusion rate of 4 reactor volumes/day will support a density of about 6 to about $8\times10^7$ cells/mL at which point cell growth approaches a stationary phase. This condition will result in reduction of culture viability and/or growth rate. To maintain cells with an optimal growth rate requires daily harvesting of reactor fluid to "cut-back" density, for example to about 3 to about $6\times10^6$ cells/mL, which is roughly equivalent to harvesting one third of a reactor volume/day. This also maintains high viability and reduces cell debris by the removal of dead cells. Most importantly, this daily harvest volume from the inside of the reactor permits removal of viral particles.

The initial step in the recovery and purification of viral particles from the daily harvest requires removal of cells and cellular debris using micro-filtration procedures. This involves use of a dead-end filtration device utilizing a membrane with a pore size in the range of about 0.65 to about 0.8 microns. This procedure serves to separate the cells and cell debris from the viral particles.

This procedure typically involves adding beta-propiolactone (BPL) to clarified harvest at a final concentration of 0.25 mL BPL per liter of supernatant, followed by incubation at 4° C. for 18–24 hours and then at 37° C. for 5 hours to inactivate the BPL. The pool is subsequently held at 4° C. for 0–6 days until further processing. This inactivation step serves to chemically reduce the infectivity of the viral particles by alkylating the various structural constituents of the virus such as lipids, proteins, nucleic acids, etc. We point out that this BPL inactivation step is not a definitive virus inactivation, and the material is still considered infectious and is treated as such.

The BPL treated material is allowed to reach ambient temperature and is concentrated 10–20 fold by tangential flow ultrafiltration using a 300,000 MW cutoff membrane. The concentrated pool is then diafiltered against 5–10 volumes of phosphate buffered saline (PBS), pH 7.5. The pore size of the membrane used in this step serves to retain HIV particles while removing greater than 90% of human serum albumin and other proteins from the growth medium, and other relatively small molecules in the permeate.

The pH of the concentrated and diafiltered material is adjusted to pH 7.5 and is loaded onto a column containing TMAE FRACTOGEL (tentacle anion exchange resin) resin at a linear flow rate of 50 cm/hr. The column is washed with approximately 3–5 column volumes of 0.5 M NaCl pH 6.5. Bound product is then eluted using 1.0 M NaCl pH 6.5, and the entire peak absorbing at 280 nm is collected. The column is subsequently sanitized following a 1–2 column volume wash with 1.0 N NaOH. The product contained in the 1.0 M NaCl elution fraction is diluted six fold to reduce the salt concentration to within the range 0.1–0.2 M NaCl and pH 6.5–7.5. It is then applied to a Q-SEPHAROSE FAST FLOW (quaternary amine beaded agarose) column which contains approximately one half the amount of resin compared to the TMAE FRACTOGEL (tentacle anion exchange resin) column at a linear flow rate of 100 cm/hr. The column is washed with 3–5 column volumes of 0.6 M NaCl pH 6.5. The bound product is eluted again using the 1.0 M NaCl buffer.

The 1.0 M NaCl fraction from the Q-SEPHAROSE FAST FLOW (quaternary amine beaded agarose) column is concentrated approximately 5 fold using an ultrafiltration plate and frame device containing a 100,000–300,000 MW cut-off membrane. The concentrate is then diafiltered against PBS pH 7.5 to reduce the salt concentration. To minimize product loss in dead space following concentration, the equipment is flushed with 1 dead space volume of saline (0.9% NaCl) and the wash is added to the diafiltered fraction. The material is frozen at –70° C., and is subjected to cobalt irradiation (2 to 4.5 megarads for approximately 24 hours), which serves as a final viral inactivation step.

At this stage the preformulated product is diluted with 0.9% saline for injection to achieve the required concentration of antigen (p 24 concentration), and is aseptically mixed with an equal volume of Incomplete Freund's Adjuvant using a shaker device for approximately 15–20 minutes.

Figure 3:
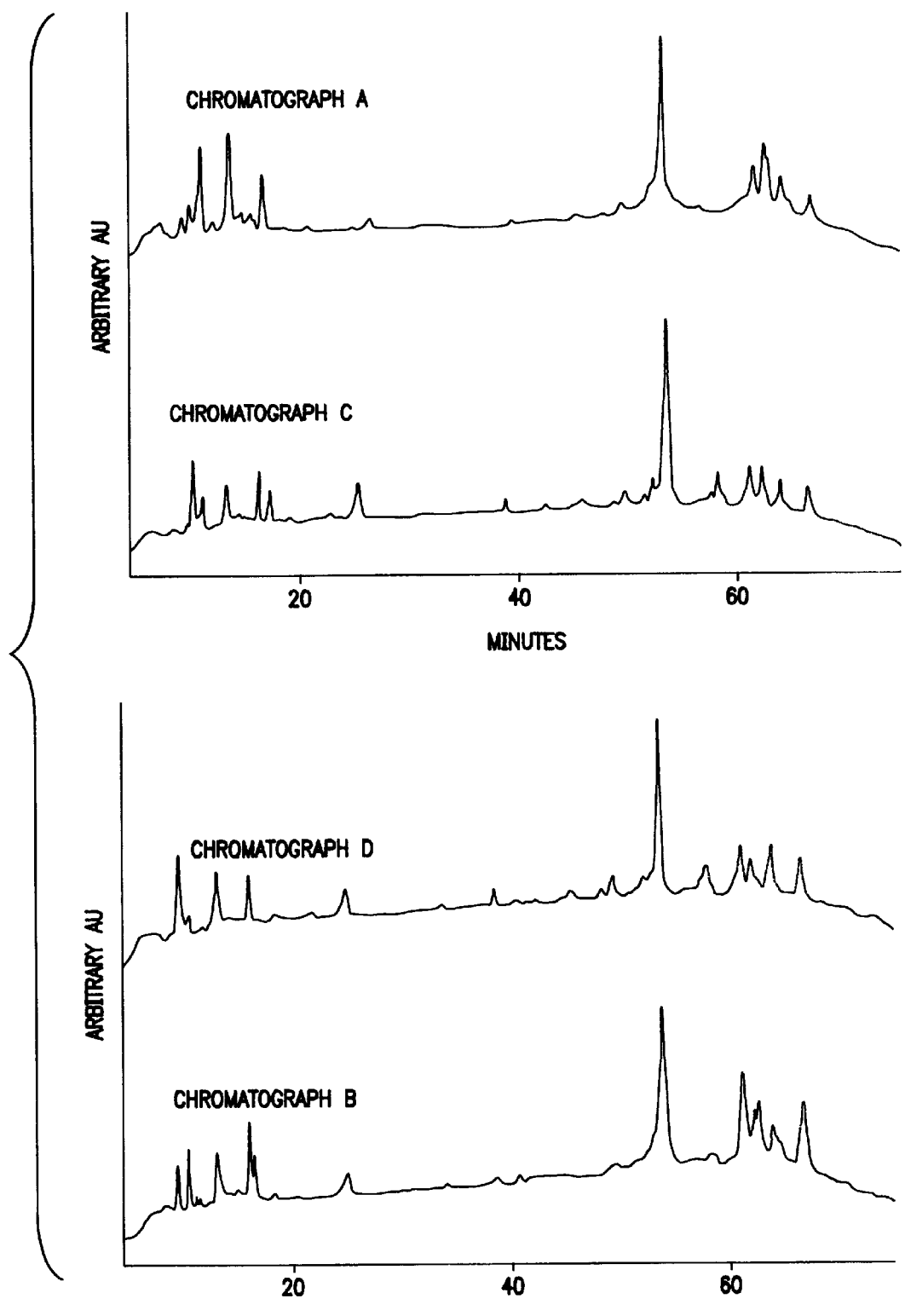
FIG. 3 shows fractionation chromatographs of HIV-1 on a C4 reverse phase HPLC column (Vydac®) for the following: the reference standard lot of HIV-1 particles prepared by the "Classical Process" multiple batch culture system (Chromatograph A); a lot of HIV-1 particles prepared by the "Classical" multiple batch culture system (Chromatograph B); and two lots of HIV-1 particles prepared by the perfusion bioreactor system (Chromatographs C and D). Each chromatograph is for approximately 100 μg of product that was denatured by heating to 80° C. for 15 minutes in 6 M guanidine-HCl (Gu-HCl) and 10 mM dithiothreitol (DTT). The elution patterns were obtained using a gradient of acetonitrile at a flow rate of 1 mL/minute Measured against Arbitrary Absorbance Units (AU).
Figure 5:
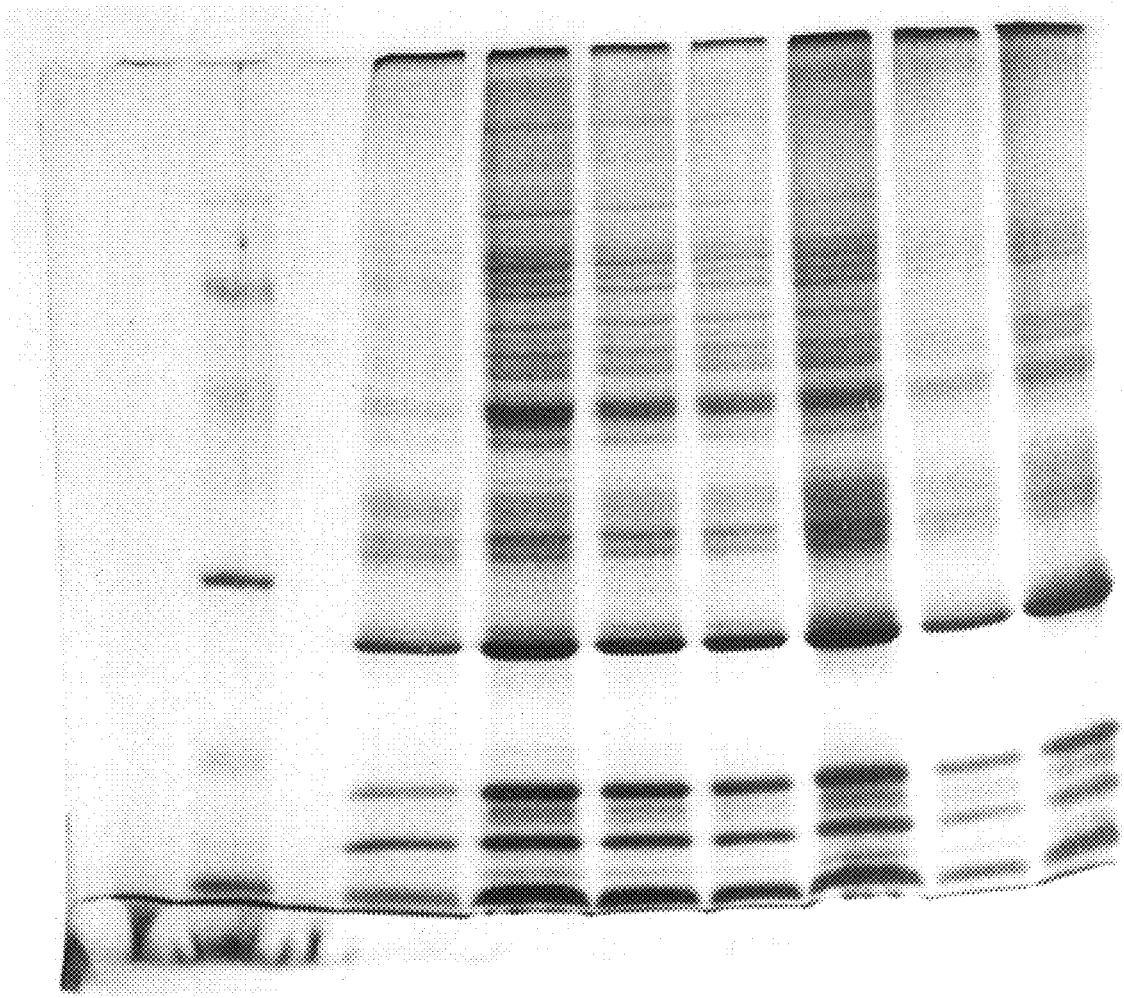
FIG. 5 is an SDS Page that shows the staining profile for the reference standard lot of HIV-1 particles prepared by the "Classical Process" (lane 7), the staining profile of HIV-1 particles isolated from the final harvest of a perfusion bioreactor system that was operated for five weeks (lane 6) and the staining profiles of HIV-1 particles isolated from harvest during the first, second, third, fourth and fifth weeks the perfusion bioreactor system's operation (lanes 1–5 respectively) and the staining profile for low molecular weight markers (lane 8).

The work includes the characterization of HIV-1 depleted of gp 120 prepared according to the invention which is essential for establishing a new reference standard for controlling lot to lot consistency and to demonstrate comparability to material prepared by the "Classical Process". Characterization data shows product comparability to material prepared by the batch culture/sucrose gradient methodology by using known HPLC (FIG. 3), Western Blot (FIG. 4) and SDS-Page (FIG. 5) procedures, product consistency whether isolated from starting material at the beginning or end of the bioreactor run Western Blot (FIG. 4), and product consistency between different bioreactor runs HPLC (FIG. 3).

Figure 6:
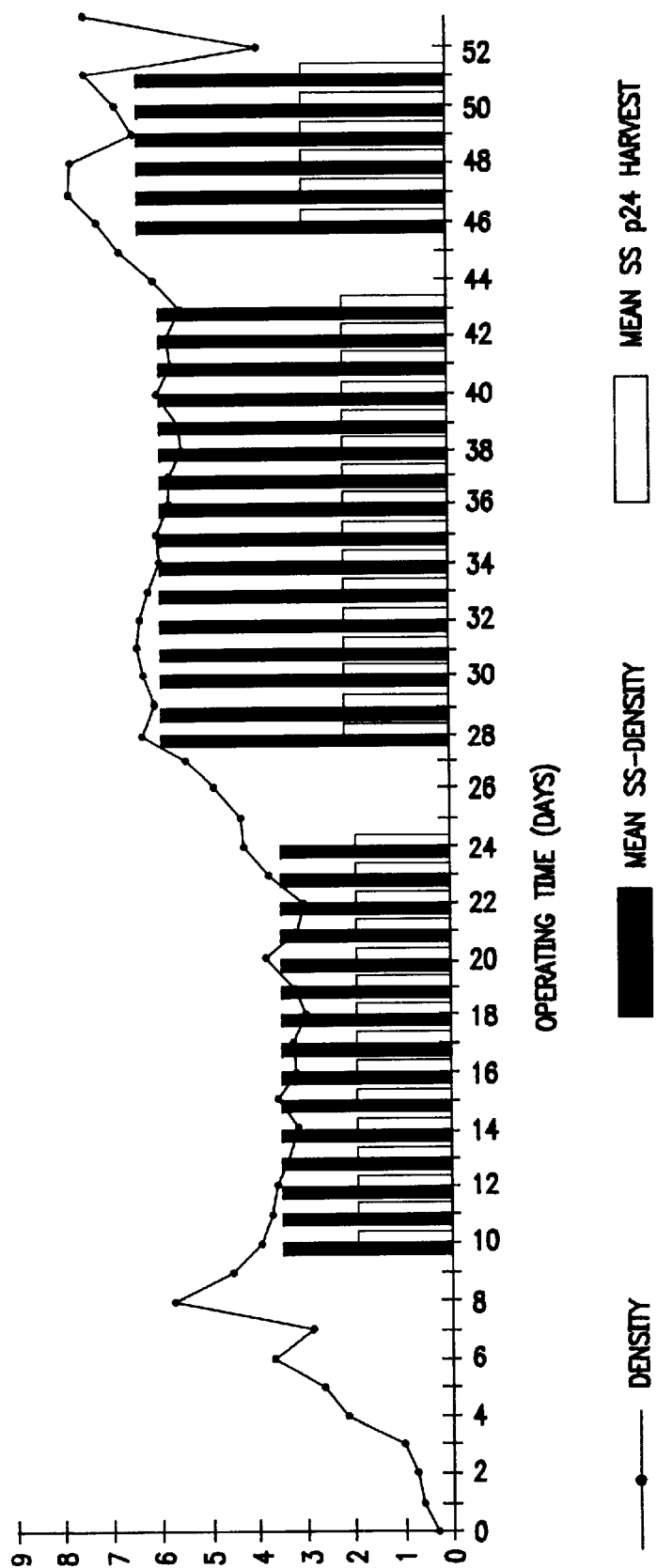
FIG. 6 shows a 52 day perfusion bioreactor run for growing HIV infected cells with concomitant HIV-1 production wherein three steady state conditions were maintained, between days 10 to 24, days 28 to 43, and finally days 46 to 51. The measure of productivity, p24 concentration, is shown as a function of average cell density for the three phases of steady-state (SS) conditions.

The performance of a typical bioreactor run (FIG. 6) shows a growth phase lasting to day 6 at which time the production phase is started by beginning daily cell harvest. The production phase lasts 48 days. FIG. 6 shows that the bioreactor is maintained at three different steady state cell densities by controlling the harvest volume. In this run (FIG. 6) steady state cell density is maintained at approximately $3.5 \times 10^6$ cells/mL between day 10–24; approximately $6 \times 10^6$ cells/mL between days 28–43; and approximately $7 \times 10^6$ between days 46–51. The measure of productivity, p24 concentration, is shown as a function of average cell density for each steady state period. Clearly, higher cell densities increase yield of p24. In addition, a faster growth rate is desirable as this requires a larger harvest volume to maintain a steady state cell density. Since product is recovered from the daily cell harvest, this translates into higher daily output of viral particles.

What is claimed is:

1. A process for purifying viral particles comprising contacting said viral particles with a tentacle anion exchange resin and eluting said viral particles from said tentacle anion exchange resin.

2. The process of claim 1, further comprising contacting said viral particles with a quaternary amine resin and eluting said viral particles from said quaternary amine resin.

3. The process of claim 2, wherein the quaternary amine resin is a Q-SEPHAROSE (quaternary amine beaded agarose) resin.

4. The process of claim 1, wherein said eluting is carried out with about 0.6 to about 2 M NaCl.

5. The process of claim 1, wherein said eluting is carried out with about 1 M NaCl.

6. The process of claim 1, wherein said tentacle anionic exchange resin is TMAE FRACTOGEL (tentacle anion exchange resin).

7. The process of claim 1, wherein said purifying further comprises washing said tentacle anion exchange resin with about 0.1 to about 0.55 M NaCl after said contacting and before said eluting.

* * * * *